United States Patent
Lahr et al.

(10) Patent No.: US 8,191,413 B2
(45) Date of Patent: Jun. 5, 2012

(54) METHOD FOR DETERMINING THE NITROGEN DIOXIDE CONCENTRATION IN EXHAUST GASES

(75) Inventors: Jochen Lahr, Stuttgart (DE); Rainer Pauls, Vaihingen (DE)

(73) Assignee: Daimler AG, Stuttgart (DE)

( * ) Notice: Subject to any disclaimer, the term of this patent is extended or adjusted under 35 U.S.C. 154(b) by 108 days.

(21) Appl. No.: 12/864,189

(22) PCT Filed: Dec. 20, 2008

(86) PCT No.: PCT/EP2008/010973
§ 371 (c)(1), (2), (4) Date: Jul. 22, 2010

(87) PCT Pub. No.: WO2009/092429
PCT Pub. Date: Jul. 30, 2009

(65) Prior Publication Data
US 2010/0293925 A1  Nov. 25, 2010

(30) Foreign Application Priority Data
Jan. 23, 2008  (DE) .......................... 10 2008 005 640

(51) Int. Cl.
*G01M 15/10* (2006.01)
(52) U.S. Cl. .................................. 73/114.71; 73/23.33
(58) Field of Classification Search ...... 73/23.31–23.33, 73/114.69, 114.71, 114.73, 114.75
See application file for complete search history.

(56) References Cited

U.S. PATENT DOCUMENTS

| | | | |
|---|---|---|---|
| 5,426,934 A | 6/1995 | Hunt et al. | |
| 5,624,640 A | 4/1997 | Potthast et al. | |
| 6,062,064 A * | 5/2000 | Yoshida et al. | 73/23.2 |
| 6,079,203 A * | 6/2000 | Wakamoto | 60/274 |
| 6,378,295 B1 | 4/2002 | Heinze | |
| 6,592,732 B1 * | 7/2003 | Komachiya et al. | 204/426 |
| 7,051,519 B2 * | 5/2006 | Kuboshima et al. | 60/286 |
| 7,319,928 B2 | 1/2008 | Hodjati et al. | |

(Continued)

FOREIGN PATENT DOCUMENTS
DE 44 02 850 A1 8/1994
(Continued)

OTHER PUBLICATIONS

International Search Report including partial English translation dated May 8, 2009 and PCT/ISA/237 Form (Fourteen (14) pages).

(Continued)

*Primary Examiner* — Freddie Kirkland, III
(74) *Attorney, Agent, or Firm* — Crowell & Moring LLP

(57) ABSTRACT

In a method for determining an $NO_2$ concentration and/or a concentration ratio of $NO_2$ and NO in an exhaust tract of a combustion device, such as an internal combustion engine, an NOx sensor that is sensitive with respect to $NO_2$ and NO is utilized, which provides a NOx output signal correlating with an NOx concentration representing the sum of the concentrations of $NO_2$ and NO. In order to determine the $NO_2$ concentration and/or the concentration ratio of $NO_2$ and NO, the NOx output signal of a first NOx sensor, which is arranged upstream of an exhaust gas treatment element arranged in the exhaust tract and having the capability of converting NO to $NO_2$ and/or converting $NO_2$ to NO, is compared to the NOx output signal of a second NOx sensor, which is disposed downstream of the exhaust gas treatment element.

16 Claims, 1 Drawing Sheet

U.S. PATENT DOCUMENTS

| | | |
|---|---|---|
| 7,624,628 B2 * | 12/2009 | Bartley ................... 73/114.75 |
| 2006/0021334 A1 * | 2/2006 | Kuboshima et al. ............ 60/295 |
| 2006/0039826 A1 * | 2/2006 | Nakatani et al. ............ 422/68.1 |
| 2007/0089406 A1 | 4/2007 | Doring |
| 2007/0150162 A1 * | 6/2007 | Hodjati et al. ................ 701/102 |
| 2009/0158813 A1 * | 6/2009 | Bartley ....................... 73/23.31 |

FOREIGN PATENT DOCUMENTS

| | | |
|---|---|---|
| DE | 43 34 672 A1 | 4/1995 |
| DE | 198 19 204 C1 | 9/1999 |
| DE | 10 2006 049 655 A1 | 4/2007 |
| EP | 0 723 662 B1 | 7/1996 |
| EP | 0 820 799 A2 | 1/1998 |
| EP | 0 869 359 A2 | 10/1998 |
| EP | 1 174 712 A1 | 1/2002 |
| EP | 1 628 133 A1 | 2/2006 |
| FR | 2 864 146 A1 | 6/2005 |

OTHER PUBLICATIONS

Corresponding European Office Action dated Dec. 17, 2010 (Four (4) pages).

Ioannis P. Kandylas, et al.,"Diesel Soot Oxidation with $NO_2$: Engine Experiements and Simulations", Ind. Eng. Chem. Res., 2002, pp. 5372-5384, vol. 41, American Chemical Society.

* cited by examiner

METHOD FOR DETERMINING THE NITROGEN DIOXIDE CONCENTRATION IN EXHAUST GASES

This application is a national stage of PCT International Application No. PCT/EP2008/010973, filed Dec. 20, 2008, which claims priority under 35 U.S.C. §119 to German Patent Application No. 10 2008 005 640.5, filed Jan. 23, 2008, the entire disclosure of which is herein expressly incorporated by reference.

The present invention relates to a method for determining a nitrogen dioxide concentration and/or a concentration ratio of nitrogen dioxide and nitrogen monoxide in an exhaust tract of a combustion device.

In German patent document DE 10 2005 049 655 A, the important role of nitrogen dioxide ($NO_2$) as a reaction partner is indicated in a plurality of reactions with an aftertreatment of internal combustion engine exhaust gas. On the other hand, $NO_2$ is a toxic exhaust gas component, whose release should be avoided if possible. It is correspondingly suggested to adjust the $NO_2$ content in the exhaust gas in a suitable manner. The activity of a catalyst arranged in the exhaust tract with the capability for the oxidation of nitrogen monoxide (NO) to $NO_2$ is hereby influenced, which takes place by variation of the part of materials, which compete with the said oxidation reaction. A sensory $NO_2$ determination is suggested amongst others for controlling the method. However, presently conventional sensors for the selective determination of NOx are not suitable (or suitable only with difficulty) for a practical use in the exhaust gas of combustion devices. Conventional sensors used for measuring the concentration of nitrogen oxides (NOx) in the exhaust gas rather have a sensitivity towards NO and also towards $NO_2$, so that one cannot distinguish between these two nitrogen oxides. On the other hand, it is desirable according to the previously described circumstance in many respects to have available a signal representing the $NO_2$ content in the exhaust gas.

It is thus one object of the invention to give a method which enables a determination of $NO_2$ concentration and/or a concentration ratio of $NO_2$ and NO in exhaust gases of combustion devices which is as reliable as possible.

This and other objects and advantages are achieved by the method according to the invention for determining a nitrogen dioxide concentration and/or a concentration ratio of nitrogen dioxide and nitrogen monoxide in an exhaust tract of a combustion device (in particular an internal combustion engine) in which a nitrogen oxide sensor that is sensitive with regard to nitrogen monoxide and nitrogen dioxide provides a nitrogen oxide output signal that correlates with a total nitrogen oxide concentration represented by the sum of the concentration of nitrogen monoxide and nitrogen dioxide. For determining the nitrogen dioxide concentration and/or the concentration ratio of nitrogen dioxide and nitrogen monoxide, the nitrogen oxide output signal of a first nitrogen oxide sensor which is arranged upstream of an exhaust gas treatment system arranged in the exhaust tract with the capability for converting nitrogen monoxide to nitrogen dioxide and/or for converting nitrogen dioxide to nitrogen monoxide is thereby compared to the nitrogen oxide output signal of a second nitrogen oxide sensor, which is arranged downstream of the exhaust gas treatment element. With a reference to nitrogen monoxide or nitrogen dioxide, the designations "NO" and "$NO_2$" are used, while, with a summary reference to nitrogen oxide comprising NO and $NO_2$, the designation "NOx" is used, or nitrogen oxide is mentioned in general.

In particular with the knowledge or assumption of certain boundary conditions at the location of the first nitrogen oxide sensor (for example a predetermined Nox concentration and/or a predetermined concentration ratio of NO and $NO_2$, and/or a predetermined $NO_2$ concentration), the concentration ratio of NO and $NO_2$ and/or the $NO_2$ concentration can be determined at the location of the second nitrogen oxide sensor by comparing the output signals of the two nitrogen oxide sensors. This is of importance in that, starting from a mainly negligible $NO_2$ concentration in the exhaust gas discharged directly from the combustion device, the concentration ratio of NO and $NO_2$ and/or the $NO_2$ concentration generally changes when passing exhaust gas treatment elements arranged in the exhaust tract. The NOx concentration can remain unchanged thereby. Such a change can also occur without the influence of an exhaust gas treatment component alone due to the predetermined thermodynamic boundary conditions. A naturally occurring oxidation from NO to $NO_2$ takes place for example with the presence of free oxygen.

The method according to the invention can be used with advantage with combustion engines of motor vehicles, especially with combustion engines operated at least periodically with an air excess, such as Diesel or lean Otto engines. Correspondingly, the exhaust gas treatment element can be an exhaust gas catalyst as for example an oxidation, denox, or three-way catalyst or a catalytically coated or uncoated particle filter. A capability for influencing the $NO_2$ concentration and/or the concentration ratio of NO and $NO_2$ can be effected by a property that can be directly attributed to the exhaust gas treatment element or by a property caused by materials supplied with the exhaust gas or by deposits. For example, in a particle filter flown through by exhaust gas, soot deposited thereon can reduce $NO_2$ to NO, or an oxidation of NO to $NO_2$ can take place in an oxidation catalyst flown through by exhaust gas. Furthermore, the amount of the $NO_2$ concentration or the concentration ratio of $NO_2$ and NO has influence on the course of the relevant reactions with many exhaust gas treatment methods, as for example with the selective catalytic Nox reduction by means of ammonia, hydrogen or hydrocarbon. By means of the determination of the $NO_2$ concentration and/or a concentration ratio of $NO_2$ and NO according to the invention, a soot charge of a particle filter or an effectiveness of a SCR exhaust gas aftertreatment method can therefore for example be determined or modeled, or characteristic numbers of an implemented reaction model can be adapted and the operation of a corresponding exhaust gas aftertreatment system can thus be improved.

The nitrogen oxide sensor can be a sensor of a known design, for example on the basis of a solid electrolyte or a semiconductor sensor. Corresponding sensors are for example described in German patent document DE 198 19 204 C1 and DE 43 34 672 A1, and European patent documents EP 0 820 799 A2 and EP 0 723 662 B1. Generally, a nitrogen oxide sensor can be used according to the invention, which provides a nitrogen oxide output signal, which correlates with a total NOx concentration represented by the sum of the concentrations of NO and $NO_2$. This nitrogen oxide output signal will typically be the only one which is relevant with regard to an output signal. This does however not exclude that the nitrogen oxide sensor can provide one or several further output signals, which correlate with the concentration of another exhaust gas component as e.g., oxygen or an exhaust gas state parameter as for example the exhaust gas temperature.

In the arrangement of the method according to the invention, nitrogen oxide sensors of the same design are used as first and second nitrogen oxide sensor. The component effort is reduced in this manner and cost advantages can be achieved.

In a further advantageous arrangement of the invention, nitrogen oxide sensors are used as the first and the second nitrogen oxide sensor, which have different nitrogen oxide output signal characteristics with regard to NO and $NO_2$. By a different sensitivity of the nitrogen oxide sensors with regard to NO and $NO_2$ at least in certain concentration regions, a more exact determination of the $NO_2$ concentration or the concentration ratio of $NO_2$ and NO is thereby enabled. It is thereby particularly advantageous if the nitrogen oxide output signal characteristics of the first nitrogen oxide sensor and of the second nitrogen oxide sensor proceed approximately in a linear manner with different gradients in a further arrangement of the method. An at least approximately linear characteristic course enables a further improvement of the exactness of the method.

In a further arrangement of the method, the $NO_2$ concentration and/or the concentration ratio of $NO_2$ and NO are determined in dependence on a difference or a ratio of the nitrogen oxide output signals of the first and the second nitrogen oxide sensor. A particularly simple, but sufficiently exact signal evaluation is thereby enabled. The output signal difference of the nitrogen oxide sensors will thereby typically again correlate with the signal ratio, so that these two operands can be can be converted into each other. Analogously, the concentration ratio of $NO_2$ and NO can typically be converted into a $NO_2$ part of the NOx concentration proportional to this.

Particularly reliable results can be achieved if the $NO_2$ concentration and/or the concentration ratio of $NO_2$ and NO at the location of the second nitrogen oxide sensor are determined starting from a predetermined total NOx concentration and/or a predetermined $NO_2$ concentration at the location of the first nitrogen oxide sensor in a further arrangement of the method.

It is also advantageous if the $NO_2$ concentration and/or the concentration ratio of $NO_2$ and NO are determined in a further arrangement of the invention under conditions in which the exhaust gas treatment element is at least approximately inactive with regard to an influence of the total NOx concentration.

In a further arrangement of the method according to the invention, an oxidation rate of soot retained in a particle filter connected downstream of the second nitrogen oxide sensor is calculated from the determined $NO_2$ concentration or the concentration ratio of $NO_2$ and NO with an oxidation-catalytically effective exhaust gas treatment element. In this manner, an improved modeling of a temporally changeable soot charge of the particle filter arranged in the exhaust tract is enabled. With a known soot deposit effect of the particle filter and for example soot emission determined from operating characteristic zones of a corresponding combustion engine, the currently accumulated soot amount in the particle filter can be determined by continuously carrying out a balance of soot amount received in and deposited from the particle filter and by oxidation of soot amount removed with $NO_2$. Points in time, where a compulsory particle filter regeneration is to be carried out by means of thermally initiated soot combustion can thus be fixed in an advantageous manner. With a serial combination of the oxidation catalyst and the particle filter connected downstream in the exhaust tract, the first nitrogen oxide sensor is preferably arranged directly in front of the oxidation catalyst for this and the second nitrogen oxide sensor is arranged between the oxidation catalyst and the particle filter.

In a further advantageous arrangement of the invention, an efficiency deterioration of the exhaust gas treatment element caused by aging is calculated from the determined $NO_2$ concentration with an oxidation-catalytically effective exhaust gas treatment element. The capability to oxidize an oxidation from NO to $NO_2$ is in many cases an indicator with regard to a damage of oxidation-catalytically effective exhaust gas treatment systems caused by ageing. For example, platinum particles of a coating of an oxidation-catalytically effective exhaust gas treatment system relevant for an oxidation effect tend to agglomeration due to thermal demands, with the result of a deteriorated catalytic effect. By means of the determination of a $NO_2$ concentration and/or a concentration ratio of $NO_2$ and NO on the output side of the exhaust gas treatment element according to the invention, the aging state of the exhaust gas treatment system can thus be determined on the corresponding values before this. A temporal adaptation of control magnitudes and process parameters of an exhaust gas aftertreatment process is thereby enabled, if a relevant change caused by ageing with regard to $NO_2$ is ascertained.

In a further arrangement of the method, a nitrogen oxide reduction efficiency of a nitrogen oxide reduction catalyst connected downstream of the second nitrogen oxide sensor is calculated from the determined $NO_2$ concentration and/or the concentration ratio of $NO_2$ and NO. In a particularly preferred version, the $NO_2$ concentration and/or the concentration ratio of $NO_2$ and NO are determined for exhaust gas flowing into a nitrogen oxide SCR catalyst or into a nitrogen oxide storage catalyst. With the exhaust gas treatment system connected upstream of this catalyst with the capability for converting NO to $NO_2$ and/or for converting $NO_2$ to NO, this can for example be an oxidation catalyst, a three-way catalyst or a catalytically coated or uncoated particle filter. The calculated nitrogen oxide reduction efficiency again enables a suitable adjustment of operating parameters for the nitrogen oxide SCR catalyst or the nitrogen oxide storage catalyst. It can for example be provided to fix a storing period of NOx or a NOx regeneration period for the nitrogen oxide storage catalyst in dependence on the nitrogen oxide reduction efficiency. An ammonia, urea or hydrocarbon supply rate can be fixed for a nitrogen SCR catalyst in dependence on the nitrogen oxide reduction efficiency. It can further be provided to define operating parameters of the combustion device with a view to a changed NOx raw emission in dependence on the nitrogen oxide reduction efficiency. With a combustion device formed as a directly injecting Diesel engine, an adjustment of points of time for a pre-injection, main injection or after-injection of fuel into the cylinders of the engine in dependence of the calculated nitrogen oxide reduction efficiency can be provided. It can of course be provided to carry out the mentioned measures and adjustments additionally or alternatively in dependence on a possibly determined aging state of one of the catalysts or an exhaust gas treatment element present in the exhaust tract additionally or alternatively.

Advantageous embodiments of the invention are described in the following with reference to a drawing. The previously mentioned characteristics which shall be explained in the following can be used not only in the respectively given characteristic combination but also in other combinations or alone without leaving the scope of the invention.

DETAILED DESCRIPTION OF THE DRAWINGS

Figure 1:
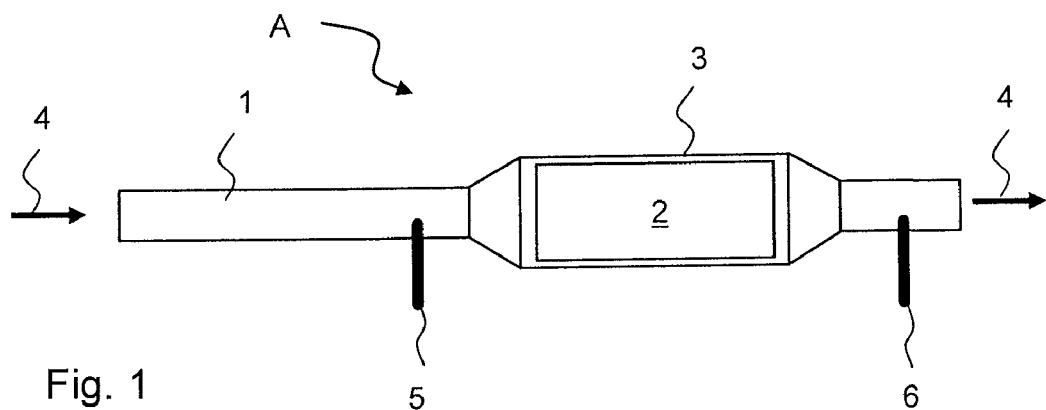
FIG. 1 is a schematic illustration of an exhaust gas treatment component arranged in an exhaust tract of a motor vehicle with a nitrogen oxide sensor connected upstream and downstream.

FIG. 1 shows a section A of an exhaust gas aftertreatment system of a motor vehicle internal combustion engine in a roughly schematic manner. With the restriction to components mainly of interest here, FIG. 1 shows an exhaust gas treatment element 2, which is arranged in an exhaust tract 1 of the internal combustion engine (not shown). The exhaust gas treatment element 2 is accommodated in a housing 3 and is flown through and/or circulated by exhaust gas from the internal combustion engine during the operation of the internal combustion engine corresponding to the arrows 4. A first nitrogen oxide sensor 5 and a second nitrogen oxide sensor 6 are arranged in the exhaust tract 1 upstream and downstream of the exhaust gas treatment element 2. The nitrogen oxide sensors 5, 6 have a sensitivity with regard to NO and $NO_2$ and respectively provide a corresponding nitrogen oxide output signal correlating with a total nitrogen oxide concentration, which is discussed in more detail below. The nitrogen oxide sensors 5, 6 are preferably those having the same design and the same sensory behavior. Nitrogen oxide sensors 5, 6 having a different design with a different sensory behavior can also be used. For the evaluation of the nitrogen oxide output signals, the nitrogen oxide sensors 5, 6 are connected to an electronic control device with a calculating function in a manner not shown.

The exhaust gas treatment element 2 has the property to be enabled for the conversion of NO to $NO_2$ and/or for the conversion of $NO_2$ to NO. For this, a plurality of different components as for example an oxidation catalyst, a reduction catalyst, a particle filter charged with soot, or possibly another component are considered. Further exhaust gas treatment components or components as for example a particle filter and/or a SCR, three-way, nitrogen oxide storage or oxidation catalyst, further exhaust gas sensors, as for example lambda sensors or temperature sensors can be connected upstream or downstream of the exhaust gas treatment system 2 (not shown).

In the following, it is assumed (without restricting the generality) that the exhaust gas treatment element 2 is an oxidation catalyst, which is arranged as a first exhaust gas treatment system flown through by exhaust gas near the internal combustion engine in the exhaust tract 1 and thus is charged with exhaust gas, which has experienced only negligible or no changes with regard to its original composition.

In the following, it is further gone into detail in which manner the $NO_2$ concentration and/or the concentration ratio of $NO_2$ and NO can be determined especially at the location of the second nitrogen oxide sensor 6 for the evaluation or control or regulation of an exhaust gas cleaning process generally provided in the exhaust tract 1, which has elapsed or elapses during or after the passing of the exhaust gas treatment element 2, by comparison of the nitrogen oxide output signals of the nitrogen oxide sensors 5, 6. The basis for this is the fact assumed in the following that the nitrogen oxide sensors 5, 6 respectively have different sensitivities for NO and $NO_2$. The corresponding characteristics can in principle be formed in a virtually arbitrary manner.

Figure 2:
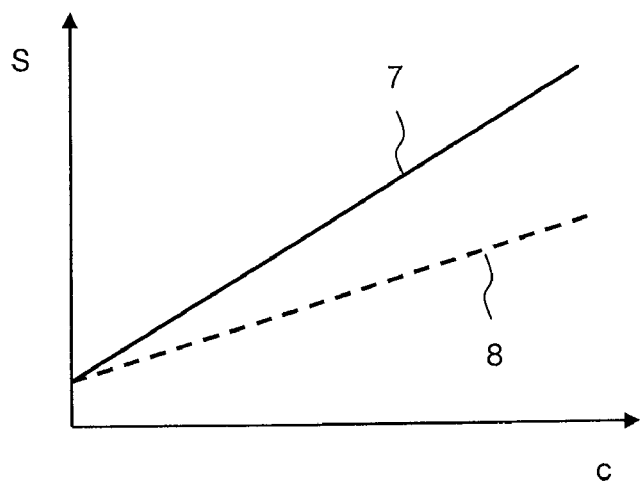
FIG. 2 is a characteristic diagram for the clarification of an output signal characteristic for a typically used nitrogen oxide sensor.

With reference to FIG. 2, an advantageous procedure is explained in the following without restricting the generality, which is preferably used with approximately linear nitrogen oxide output signal characteristics of the first nitrogen oxide sensor 5 and the second nitrogen oxide sensor 6. In the diagram of FIG. 2, the dependencies S=S(c) of the nitrogen oxide output signals S of the nitrogen oxide sensors 5, 6 of the concentration c of NO or $NO_2$ are shown. The characteristic denoted with 7 shall be the relevant characteristic in an exemplary manner, while the characteristic with a lower gradient denoted with 8 shall be relevant for $NO_2$. The reverse case is naturally also possible. A nitrogen oxide output signal S provided by one of the nitrogen oxide sensors 5, 6 thus generally has a first part, which is caused by the NO concentration, and a second part, which is caused by the $NO_2$ concentration in the exhaust gas. It can thereby initially not be assessed in which measure each of these parts contribute to the nitrogen oxide output signal S correlating with the total nitrogen oxide concentration. Due to the comparison of the nitrogen oxide output signals S of the nitrogen oxide sensors 5, 6 conducted according to the invention, especially in the case of a predetermined boundary condition, the $NO_2$ concentration and/or the concentration ratio of $NO_2$ and NO can be determined at the location of the second nitrogen oxide sensor 6 can however be determined. In simple cases, a comparison in the form of a difference or ratio formation is sufficient. The comparison can however also contain more complex, for example non-linear calculation and approximation methods or the like. If it is for example assumed that the $NO_2$ concentration in the exhaust gas at the location of the first nitrogen oxide sensor 5 is negligible, as is e.g., regularly the case with an arrangement of the exhaust gas treatment element 2 near the internal combustion engine, the following relations result, if the total nitrogen oxide concentration in the exhaust gas is not influenced by the exhaust gas treatment element 2 and nitrogen oxide sensors 5, 6 with the same nitrogen oxide output signal characteristics 7, 8 are used:

$$c_{5NO}*m_7=S_5 \quad (1)$$

$$c_{6NO}*m_7+c_{6NO2}*m_8=S_6 \quad (2)$$

$$c_{5NO}-c_{6NO}-c_{6NO2}=0 \quad (3).$$

$c_{5NO}$, $c_{6NO}$, $c_{6NO2}$ thereby denote the concentrations c of NO and $NO_2$ at the locations of the nitrogen oxide sensors 5, 6, $m_7$, $m_8$ gradients of the nitrogen oxide output signal characteristics 7, 8, and $S_5$, $S_6$ the nitrogen oxide output signals of the nitrogen oxide sensors 5, 6.

From the equations (1) to (3), the following linear relation results between the $NO_2$ concentration $c_6NO_2$ at the location of the second nitrogen oxide sensor 6 and the difference of the nitrogen oxide output signals S of the nitrogen oxide sensors 5, 6:

$$c_{NO2}=(S_6-S_5)/(m_8-m_7). \quad (4)$$

Figure 3:
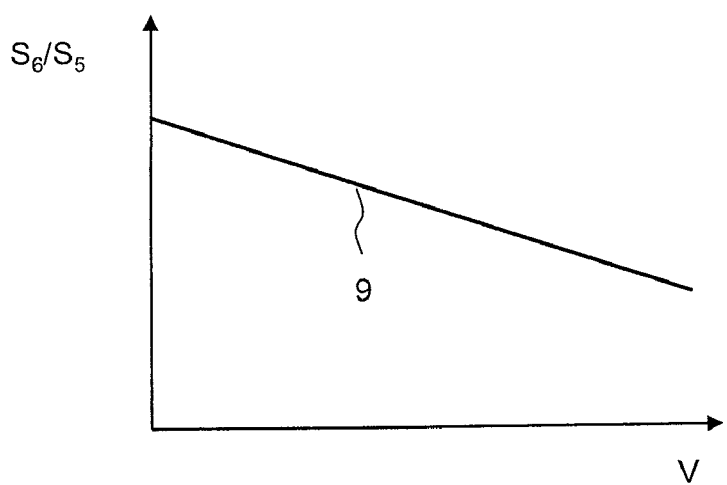
FIG. 3 is a diagram for the clarification of information obtained by the combination of output signals of two nitrogen oxide sensors.

Other relations can also be derived with modified calculation procedures. FIG. 3 shows for example a diagram with a dependence of the ratio $S_6/S_5$ of the nitrogen oxide output signals $S_5$, $S_6$ of the nitrogen oxide sensors 5, 6 given by the curve 9 of a ratio V of $NO_2$ concentration and NOx concentration at the location of the second nitrogen oxide sensor 6. A linear relation also results with the above-mentioned assumptions. A ratio of the concentration of $NO_2$ and NO in dependence on a combination of the nitrogen oxide output signals $S_5$, $S_6$ of the nitrogen oxide sensors 5, 6 can analogously be determined. The mentioned magnitudes are preferably determined in real time from the nitrogen oxide output signals $S_5$, $S_6$ provided by the nitrogen oxide sensors 5, 6. A fallback to previously determined data and which are provided in the form of value tables or characteristics corresponding to FIG. 2 is thereby advantageous. A plausibility calibration with stored and available data for the NOx raw emission of the internal combustion engine for different operating points or regions is furthermore advantageous.

It is obvious that the calculation methods described above only in an exemplary manner can be used in a modified form, if other predetermined boundary conditions are assumed.

It can also be provided to modify the arrangement shown in FIG. 1. Two or several separate components can for example be provided as exhaust gas treatment element 2. These can be arranged behind each other in series or parallel to each other. Three or more nitrogen oxide sensors can thereby also be used, whereby a plurality of $NO_2$ concentrations and/or concentration ratios of $NO_2$ and NO can be determined at different locations in the exhaust tract 1.

The data concerning a $NO_2$ concentration and/or a concentration ratio of $NO_2$ and NO which are determined according to a procedure according to the invention can be further processed in a multiple manner. Further information regarding the state and the effectiveness of further exhaust gas cleaning components arranged in the exhaust tract 1 can thereby be determined and/or the operation of exhaust gas cleaning components can be controlled or regulated.

For example, the aging state or a damage of an exhaust gas treatment element 2 in particular with predetermined operating conditions can be determined by means of comparison with reference values. This can especially be provided for an exhaust gas treatment element 2 formed as an oxidation catalyst, as the capability for the NO oxidation decreases with damage caused by ageing with usual oxidation catalysts. This can analogously also be carried out for an exhaust gas treatment system 2, which can convert NOx to $N_2$ in a reductive manner. An exhaust gas treatment element 2 formed as a SCR catalyst can for example be diagnosed. It is advantageous for this intended use to interrupt an otherwise provided supply of a reduction means provided for the NOx reduction in a diagnostics operating mode. It is achieved thereby that the SCR catalyst is inactive with regard to an influencing of the total nitrogen concentration during the diagnostics.

It can further be provided to use the determined data for determining a soot charge of an exhaust gas treatment element 2 formed as a soot particle filter. It is particularly advantageous for this to sense a reduction of the $NO_2$ concentration in the exhaust gas taking place due to an oxidation of soot by reaction with $NO_2$ when passing the exhaust gas cleaning element 2 formed as a soot particle filter in the manner according to the invention.

It can further be provided to use the data for the $NO_2$ concentration in the exhaust gas determined according to the invention for controlling or regulating the operation of a SCR catalyst. It is advantageous for this to make available a usually given dependence of a NOx reduction efficiency from the $NO_2$ concentration or from the ratio of $NO_2$ and NO in the form of a characteristic zone or a characteristic and to adjust a reduction means supply in dependence on the current $NO_2$ concentration values or on the catalyst efficiency depending thereon.

It can also be provided to monitor a $NO_2$ concentration in the exhaust gas immediately prior to its output to the environment (tail pipe emission) using the method according to the invention. It is convenient for this to provide nitrogen oxide sensors 5, 6 on the input and output side of an exhaust gas treatment element 2 provided at the end side in the exhaust gas system in the exhaust gas flow direction 4.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

The invention claimed is:

1. A method for calculating an oxidation rate of soot retained in a particle filter that is arranged in an exhaust tract of a combustion device, downstream of an oxidation-catalytically active exhaust gas treatment element having a capability of converting nitrogen monoxide to nitrogen dioxide, using oxide sensors that are sensitive with regard to nitrogen monoxide and nitrogen dioxide, and that provide a nitrogen oxide output signal correlating with a total nitrogen oxide concentration representing the sum of the concentration of nitrogen monoxide and nitrogen dioxide; said method comprising:

determining one of a nitrogen dioxide concentration and a concentration ratio of nitrogen dioxide and nitrogen monoxide downstream of said oxidation-catalytically active exhaust gas treatment element and upstream of said particle filter in said exhaust gas tract, by comparing a nitrogen oxide output signal of a first nitrogen oxide sensor that is arranged upstream of said oxidation-catalytically active exhaust gas treatment element in said exhaust gas tract, with a nitrogen oxide output signal of a second nitrogen oxide sensor that is arranged downstream of said oxidation-catalytically active exhaust gas treatment element and upstream of said particle filter in said exhaust gas tract; and calculating said oxidation rate of soot from the determined nitrogen dioxide concentration or concentration ratio of nitrogen dioxide and nitrogen monoxide.

2. The method according to claim 1, wherein nitrogen oxide sensors of the same design are used as the first and second nitrogen oxide sensors.

3. The method according to claim 1, wherein:
nitrogen oxide sensors used as the first and second nitrogen oxide sensors have different nitrogen oxide output signal characteristics with regard to nitrogen monoxide and nitrogen dioxide.

4. The method according to claim 3, wherein the nitrogen oxide output characteristics of the first nitrogen oxide sensor and of the second nitrogen oxide sensor proceed approximately in a linear manner, with different gradients.

5. The method according to claim 1, wherein said one of a nitrogen dioxide concentration and a concentration ratio of nitrogen dioxide and nitrogen monoxide is determined in dependence on a difference or a ratio of the nitrogen oxide output signals of the first and the second nitrogen oxide sensor.

6. The method according to claim 1, wherein the nitrogen dioxide concentration or the concentration ratio of nitrogen dioxide and nitrogen monoxide is determined at the location of the second nitrogen oxide sensor starting from a predetermined total nitrogen oxide concentration and/or a predetermined nitrogen dioxide concentration at the location of the first nitrogen oxide sensor.

7. The method according to claim 1, wherein a temporarily changeable soot charge of the particle filter is calculated base on the oxidation rate of soot retained in the particle filter.

8. The method according to claim 1, wherein points in time, where a compulsory regeneration of the particle filter is to be carried out by means of thermally initiated soot combustion, are calculated.

9. A method, comprising:
determining one of a nitrogen dioxide concentration and a concentration ratio of nitrogen dioxide and nitrogen monoxide downstream of an oxidation-catalytically active exhaust gas treatment element and upstream of a particle filter in an exhaust gas tract, by comparing a nitrogen oxide output signal of a first nitrogen oxide sensor arranged upstream of said oxidation-catalytically active exhaust gas treatment element in said exhaust gas tract, with a nitrogen oxide output signal of a second nitrogen oxide sensor arranged downstream of said oxidation-catalytically active exhaust gas treatment element and upstream of said particle filter in said exhaust gas tract; and calculating an oxidation rate of soot retained in the particle filter from the determined nitrogen dioxide concentration or concentration ratio of nitrogen dioxide and nitrogen monoxide, wherein the first and second nitrogen oxide sensors are sensitive with regard to nitrogen monoxide and nitrogen dioxide and provide a nitrogen oxide output signal correlating with a total nitrogen oxide concentration representing the sum of the concentration of nitrogen monoxide and nitrogen dioxide.

10. The method according to claim 9, wherein nitrogen oxide sensors of the same design are used as the first and second nitrogen oxide sensors.

11. The method according to claim 9, wherein:
nitrogen oxide sensors used as the first and second nitrogen oxide sensors have different nitrogen oxide output signal characteristics with regard to nitrogen monoxide and nitrogen dioxide.

12. The method according to claim 11, wherein the nitrogen oxide output characteristics of the first nitrogen oxide sensor and of the second nitrogen oxide sensor proceed approximately in a linear manner, with different gradients.

13. The method according to claim 9, wherein said one of a nitrogen dioxide concentration and a concentration ratio of nitrogen dioxide and nitrogen monoxide is determined in dependence on a difference or a ratio of the nitrogen oxide output signals of the first and the second nitrogen oxide sensor.

14. The method according to claim 9, wherein the nitrogen dioxide concentration or the concentration ratio of nitrogen dioxide and nitrogen monoxide is determined at the location of the second nitrogen oxide sensor starting from a predetermined total nitrogen oxide concentration and/or a predetermined nitrogen dioxide concentration at the location of the first nitrogen oxide sensor.

15. The method according to claim 9, wherein a temporarily changeable soot charge of the particle filter is calculated base on the oxidation rate of soot retained in the particle filter.

16. The method according to claim 9, wherein points in time, where a compulsory regeneration of the particle filter is to be carried out by means of thermally initiated soot combustion, are calculated.

* * * * *